United States Patent [19]

Kaali et al.

[11] Patent Number: 4,616,640

[45] Date of Patent: Oct. 14, 1986

[54] BIRTH CONTROL METHOD AND DEVICE EMPLOYING ELECTRIC FORCES

[75] Inventors: Steven Kaali, Penthouse E, 225 E. 63rd St., New York, N.Y. 10021; Peter M. Schwolsky, 4101 Cathedral Ave. NW., Washington, D.C. 20016; Joseph W. Porter, Washington, D.C.

[73] Assignees: Steven Kaali, New York, N.Y.; Peter M. Schwolsky, Washington, D.C.

[21] Appl. No.: 551,590

[22] Filed: Nov. 14, 1983

[51] Int. Cl.[4] ............................................. A61F 5/46
[52] U.S. Cl. .................................. 128/130; 128/788; 429/166
[58] Field of Search ............. 128/130, 788, 127, 131, 128/784, 785, 783, 736, 738, 775, 778; 429/96, 97, 98, 163, 121, 166; 604/891

[56] References Cited

U.S. PATENT DOCUMENTS

| 353,346 | 11/1886 | Baldwin | 128/788 |
|---|---|---|---|
| 520,206 | 5/1894 | Hinkley | 128/788 |
| 662,716 | 11/1900 | Gaedeke | 128/788 |
| 3,411,507 | 11/1968 | Wingrove | 128/784 |
| 3,645,265 | 2/1972 | Majzlin | 128/788 |
| 3,901,224 | 8/1975 | Bucalo | 128/130 |
| 3,930,889 | 1/1976 | Ruggiero | 429/97 |
| 3,973,571 | 8/1976 | Sahel | 128/788 |
| 4,031,365 | 6/1977 | Raggiotti et al. | 128/738 |
| 4,194,503 | 3/1980 | Csatary | 128/130 |
| 4,515,167 | 5/1985 | Hochman | 128/738 |

Primary Examiner—Richard J. Johnson
Attorney, Agent, or Firm—Charles W. Helzer

[57] ABSTRACT

A method and device for birth control which comprises producing an electrical force within the cervical canal of a female for acting on male sperm and preventing migration of the sperm through the cervical canal and into the uterine cavity. The electrical force is provided by a self-contained, sealed battery capable by itself of producing an electromotive force and is inserted within the cervical canal and retained therein over extended periods of use. The device is designed such that it does not impede the free flow of menstrual and other discharges through the cervical canal and is fabricated with or covered by biologically inert material so that it can be retained in place in the cervical canal for indefinite periods as long as desired by the user for birth control purposes. The device is provided with anchoring means which are designed to engage the wall of the cervical canal for securely holding the device in place within the cervical canal with the electric force producing electrodes so positioned as to be exposed to fluids passing through the cervical canal.

44 Claims, 12 Drawing Figures

BIRTH CONTROL METHOD AND DEVICE EMPLOYING ELECTRIC FORCES

TECHNICAL FIELD

This invention relates to the field of birth control methods and devices for use by human females as well as the female of most quadrupeds and other vertebrates.

BACKGROUND PRIOR ART

Known methods of birth control have relied either on chemical action (i.e., birth control pills, spermicides or the like), or on mechanical means such as prophylactics, diaphragms, the interuterine device (IUD) or a combination of both chemical and mechanical means, or on permanent birth control measures such as tubaligation. While these known devices and methods for using them have been satisfactory in certain respects, there is always room for improvement in the field of birth control.

The present invention provides an entirely new approach to birth control methods and devices wherein an electric force is employed within the cervical canal of the female so that the electrical force acts on and prevents active male sperm from fertilizing female eggs thereby providing a reliable and safe form of birth control.

SUMMARY OF INVENTION

It is therefore a principal object of this invention to provide a new and improved method and device for birth control which employs the introduction of an electrical force in the female of the species in such a way as to prevent impregnation by male sperm.

More specifically, the invention provides a novel method and means of birth control employing a set of battery operated, electrically conductive electrodes which when implanted in the cervical canal of the female and activated, produces an electric force within the cervical canal. The electrical force acts upon male sperm to impede and prevent the male sperm from migrating up the cervical canal and entering the uterine cavity thereby preventing possible fertilization of a female egg in the fallopian tube.

In practicing the invention a method and device for birth control is provided which comprises producing an electrical force within the cervical canal for acting on male sperm and preventing migration of the sperm through the cervical canal and into the uterine cavity. The electrical force preferably is provided by a self-contained battery capable by itself of producing an electromotive force and which is inserted within the cervical canal and retained therein over extended periods of time. The device is designed such that it does not substantially impede the free flow of menstrual and other fluid discharges through the cervical canal and can be retained in place in the cervical canal for indefinite periods as long as desired by the user for birth control purposes.

The device includes electrically conductive electrodes supported thereon which are exposed to contact to any fluid within the cervical canal with the outer surfaces of the device and the electrically conductive electrodes being fabricated from or covered by materials which are biologically inert and safe for physical contact with human and animal tissue over extended periods of time.

The device is provided with anchoring means which are designed to engage the side of the cervical canal for securely holding the device in place within the cervical canal with the electrodes thereof so positioned as to be exposed to fluids passing through the canal.

In one embodiment, the duty cycle on the battery supplying the device is reduced by designing the electrodes so that the device is maintained in an inactive state during periods while the cervical canal is dry and no body fluids are present in the cervical canal. For this purpose the electrically conductive electrodes are placed on the battery in a position where at least one of the electrodes does not normally engage tissue. By this means the battery is maintained in an off state unless exposed to fluid passing through the cervical canal thereby reducing the duty cycle on the battery to those periods during the month when body fluids are being excreted through the cervical canal.

It is not entirely clear at this point in time what causes the electrical force to prevent the male sperm from migrating up the cervical canal. One theory is that an induced electric current is caused to flow through the mucous fluid normally discharged during midcycle by the female which in effect alters the nature of the midcycle cervical mucous such that it becomes an effective barrier to sperm transport. A second theory is that the electrical force is in the form of an electrostatic field which acts on the active male sperm (known to contain some form of electrical charge) so as to cause electrodeposition of the sperm onto the battery electrodes and preventing their further passage through the cervical canal. It is altogether possible that some combination of the two electrical forces described is involved in the effective impediment and prevention of migration of the male sperm up the cervical canal.

In a another embodiment of the invention, means are provided in the form of a microminiaturized temperature sensor for sensing the temperature of the body of the user with the temperature sensor signal being employed to connect the battery in circuit relationship across the electrodes to produce the desired electric field force upon the body temperature of the user reaching a predetermined higher temperature than normal. This predetermined higher temperature than normal, usually occurs in most females during the midcycle ovulation period while the cervical mucous fluid is present in the cervical canal.

In a further embodiment of the invention, a microminiaturized switching circuit is electrically connected in circuit relationship with the battery for periodically switching the electrodes between an inactive off condition and an on-state at a predesigned rate under conditions where the battery otherwise would be enabled to supply electricity to the electrodes to thereby reduce the duty cycle on the battery further.

In a still further embodiment of the invention, a remotely actuated switch using sound, sonar, radio wave and like signals is employed to activate the battery and place the birth control device in operation.

BRIEF DESCRIPTION OF DRAWINGS

These and other objects, features and many of the attendant advantages of this invention will be appreciated more readily as the same becomes better understood from a reading of the following detailed description, when considered in connection with the accompanying drawings, wherein like parts in each of the several figures are identified by the same reference character and wherein.

BEST MODE OF PRACTICING INVENTION

Figures 1, 2, 2A, 3, 4:
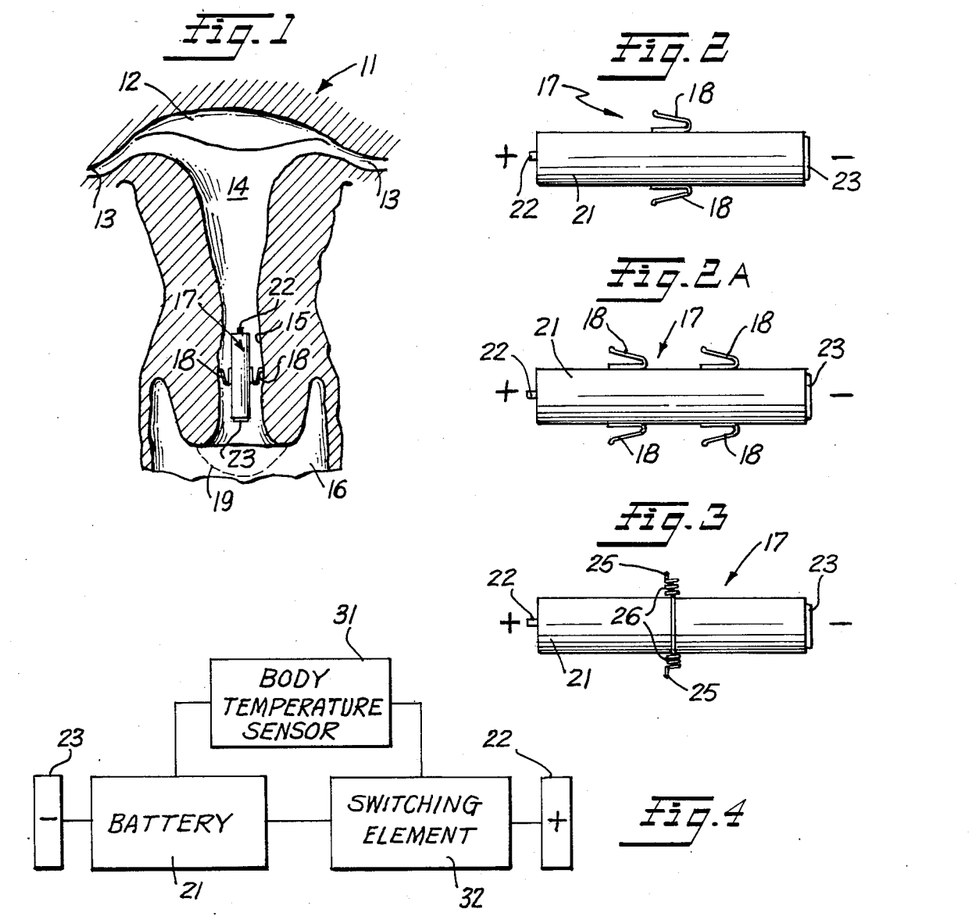
FIG. 1 is a partial schematic view of the female reproductive organs and shows the cervical canal and its relation to the uterine cavity with a birth control device constructed according to the invention implanted in the cervical canal in accordance with the novel birth control method made available by this invention.
FIGS. 2 and 2A of the drawings illustrate two forms of a birth control device constructed according to the invention of the type shown implanted in place in FIG. 1 of the drawings.
FIG. 3 illustrates an alternative construction of the anchoring means employed with the birth control device according to the invention.
FIG. 4 is a schematic block diagram showing the manner in which a microminiaturized temperature sensor employed in a particular embodiment of the invention, is connected in circuit relationship with the electric field producing electrodes and a battery supplying the electrodes.

FIG. 1 is a partial schematic view of the human female reproductive organs 11 comprised by the uterus 12, the fallopian tubes 13, the uteine cavity 14, the cervical canal 15 (also referred to as the cervix) and the vagina 16. In practicing the novel birth control method according to the present invention, a birth control device 17 for producing an electric field is implanted in the cervical canal 15. The birth control device 17 is retained in place in the cervical canal by anchoring means 18 in the form of prongs, spring-biased pins, spring retaining clips, projections from the exterior surface of the device 17 designed to engage side wall tissue of the cervical canal or other similar retaining means for anchoring the device 17 in place within the cervical canal in the manner shown in FIG. 1.

To fully understand the manner in which the birth control device 17 operates to prevent impregnation of the female's egg by a male's sperm, it is believed desirable to review briefly the reproduction process as it is presently understood. At about the midpoint of the female menstrual cycle during ovulation of the female's egg and introduction thereof through one of the fallopian tubes 13 into the uterine cavity 14, a cervical mucous in the form of a highly viscous liquid is produced in the cervical canal 15. This cervical mucous during the period of egg ovulation tends to travel down the cervical canal and form a miniscus shown at 19 between the lips of the cervical canal and which extends somewhat into the vagina. It is this miniscus of cervical mucous which tends to capture any sperm that are in the vagina and to facilitate migration of any such traped sperm upwardly through the cervical canal 15 and into the uterine cavity 14 where there is a greater probability of impregnating an egg ovulated by the female. For this to happen it will be appreciated that the cervical mucous provides a very hospitable environment to the sperm which aids and abets it in its travel up through the cervical canal and into the uterine cavity.

By the introduction of an electrical field in the cervical canal as taught in the present invention, it has been determined that the sperm cannot only be impeded in its travel upwardly through the cervical canal, but by the application of a sufficiently strong electrical force, migration of the male sperm through the cervical canal can be prevented. Thus, birth control is accomplished by the presence of the electrical force. This electrical force may be in the form of the production of an electric current flow through the cervical mucous so as to alter its characteristics such that it becomes an effective barrier to sperm transport within the cervical canal. Alternatively, the electrical force may be in the form of an electrostatic field within the cervical canal which acts directly on the sperm (known to be somewhat electrically charged) so as to electrostatically precipitate out the sperm and prevent their passage through the cervical canal. At the time of writing this disclosure it is not known which phenomenon controls or whether both phenomena are at work. However, experiments conducted have revealed that in cervical mucous exposed to an electric field having a value of say 3 volts, visual clouding of the cervical mucous being tested could be observed and sperm count from a control value in the absence of an electric force of an average of 10–12 motile sperms per field were being observed through a high power optical magnification microscope to substantially no sperms per high power field observed in the presence of a 3 volt electromotive force. In contrast, upon reduction of the electric force to 1.5 volts, tests performed after 15 minutes revealed an average of 2–4 motile sperms and occasional immotile sperms per high powered field being observed.

FIGS. 2–3 illustrate side elevational views of the construction of three different embodiments of a birth control device 17 designed for use in practicing the novel birth control method according to this invention. It should be understood, however, that the invention is not limited to the particular embodiments shown, which are disclosed solely for the purpose of illustration, and it is to be understood that the methods and devices illustrated in the drawings and described hereinafter in the specification, are only by way of example since other comparable devices for practicing the invention will be suggested to those skilled in the art in the light of applicants' disclosure.

The birth control device 17 shown in FIG. 2 comprises essentially a sealed electric battery having an elongated cylindrically-shaped body 21 which may be approximately three quarters of an inch long and one quarter of an inch in diameter. The battery itself, for example, may comprise a sealed lithium-iodine battery of the type used in heart Pacemakers, etc., having an output voltage of 2.8 volts and operating life of 0.25 ampere-hours. An electrically conductive positive electrode 22 and negative electrode 23 are formed at the respective opposite ends of battery 21 in a known manner. Spring retaining clips shown at 18 are secured to the body of battery 21 for retaining the device in place in the cervical canal as illustrated in FIG. 1. The entire assemblage of elements including the body 21, conductive electrodes 22 and 23 and the spring retaining clips 18 all are fabricated from or covered with a suitable biologically inert material, known in the art, so that the device can be implanted within female humans and animals over extended periods of time safely.

The embodiment of the invention shown in FIG. 2A is entirely similar to that shown in FIG. 2 with the notable exception that four spring retaining clips 18 are employed for anchoring the device in place within the cervical canal. Preferably, with the embodiment shown in FIG. 2A, the two sets of opposed retaining clips would be rotated ninety degrees relative to each other to assure anchoring the device within the cervical canal somewhat evenly around its periphery. If desired, additional spring clips could be employed.

FIG. 3 shows a somewhat different embodiment of the birth control device than those illustrated in FIGS. 2 and 2A. In FIG. 3, the battery body 21 is provided with spring-biased prongs 25 which are secured by biasing springs 26 to the body 21 of the battery. If desired, additional sets of opposed spring-biased prongs 25 and 26 could be added at different locations along the length of the battery body 21 and rotated some ninety degrees relative to each other so that even support for the body 21 within the cervical canal is provided.

An important physical parameter in the construction of the birth control devices shown in FIGS. 2-3, and not readily apparent from FIG. 1, is that the devices be so dimensioned that they do not substantially impede the free flow of menstrual and other fluid discharges through the cervical canal. It is for this reason that the devices are dimensioned substantially within the size range indicated in the preceeding paragraphs.

From the above brief description of the reproductive process, it will be noted that the cervical mucous is present in an hospitable form to sperm migrating through the cervical canal only during the midcycle ovulating period of each month and at other times, except during menstruation and perhaps during intercourse, the cervical canal remains substantially dry. The embodiments of the birth control device 17 shown in FIGS. 2-3 are designed such that the conductive electrodes 22 and 23 do not normally engage human tissue so that there is no closed electrically conducting path connecting the electrodes in a closed electrical circuit whereby electric current can flow from the battery between the electrodes. Thus, during a portion of each month, the batteries will be maintained in an inactive off-state whereby no electric current drain from the battery occurs. If the battery is designed so as to possess a good shelf life, then it is anticipated that it will be able to sustain itself in operation over prolonged periods since the duty cycle on the battery is greatly reduced due to the above discussed phenomenon.

To assure a sufficiently low current drain while activated, a current limiting resistor fabricated in microcircuit form can be connected in series electrical circuit relation with the electrodes in a known manner. Such a current limiting resistor could be in the form of a coating on one or both electrodes 22 and 23. Using such techniques and assuming a battery operating life of sufficient ampere hour rating, then it is possible for the battery to remain implanted in the cervical canal for periods of up to one and one-half years after which it should be removed and replaced by a gynecologist or physician. The only other time that the embodiments shown in FIGS. 2, 2A and 3 would be activated would be during the menstrual period each month for a few days; however, by providing sufficient ampere hour capacity for the battery, such intervals of activation and current drain could be accommodated.

In order to reduce the duty cycle further on the battery comprising the birth control device 17, a miniaturized body temperature sensor 31 shown in block diagram form in FIG. 4 of the drawings, can be fabricated on the exterior surface of the battery body 21 and energized thereby for sensing the body temperature of the user of the device. As is well known in medical circles, during ovulation, the body temperature of a female will be increased above normal body temperature by a known small amount. The body temperature sensor 31 senses this increase in temperature during ovulation and activates an electronic switching element 32 of miniaturized construction connected in a series electrical circuit relationship between a terminal on the end of the body of the battery 21 and an extended positive electrode member 22. Upon the switching element 32 being turned on by body temperature sensor 31, the birth control device 17 will be activated and an electrical field force created between the electrodes 22 and 23 in the previously described manner. During other periods of the month while the body temperature is at its normal value, the switching element 32 will be turned off thereby maintaining the extended electrode members 22 and 23 in an off-state during intervals such as the menstrual period and preventing a current drain from the battery during such periods.

Figure 5:
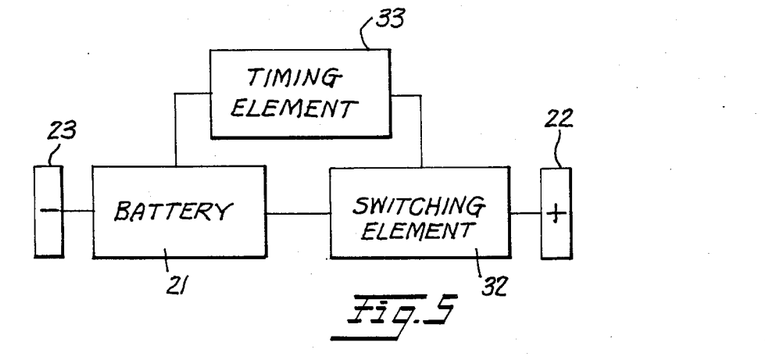
FIG. 5 is a functional block diagram of still another embodiment of the invention wherein a microminiaturized switching circuit is connected in circuit relationship between the electric field producing electrodes and the battery for periodically switching the electrodes between an active-on and an inactive-off state to thereby reduce the duty cycle on the battery.

FIG. 5 of the drawings illustrates still a further embodiment of the invention wherein a pulsed timing element of miniaturized construction and energized from the battery 21 serves to turn on and off an electronic switching element 32 of miniaturized construction connected between a terminal on the end of battery 21 and the extended electrode 22. With this arrangement, the duty cycle on the battery 21 will be reduced due to the pulsed nature of the excitation voltage being applied to the extended electrode members 22 and 23 at a pulsed switching rate determined by the timing element 33. This pulsed switching rate is established at a value which is sufficient to maintain the electrical forces acting on the sperm sufficiently strong to prevent their migration through the cervical canal.

It is of course possible for a combined device including both the body temperature sensor 31 and the timing element to be connected in series circuit relationship to control the switching element 32, as will be obvious to one of ordinary skill in the art whereby even a further reduction in duty cycle on the battery 21 can be achieved. It should be further noted, that with respect to the body temperature sensor 31, such a sensor could be remotely located elsewhere on the body of the user and its output temperature responsive signal supplied to the switching element 32 through an appropriate insulated conductor having a diameter about the size of a string. The remote body temperature sensor would be secured to the body of the user externally with the string-like conductor leading up into the cervical canal to the birth control device 17 which includes a miniaturized switching element 32. A doctor could use the string-like conductor to assist in extraction of the birth control device when it is desirable to remove the device from the body of a user. Other similar variations will be suggested to those skilled in the art. For example, the electric force producing battery 21 itself could be mounted externally of the body of the user, and the excitation voltage supplied therefrom to a set of normally inert electrodes (to be described hereinafter) mounted within the cervical canal by suitable insulated conductive wires of string-like dimensions and flexibility.

Figures 6, 6A, 6B, 7:
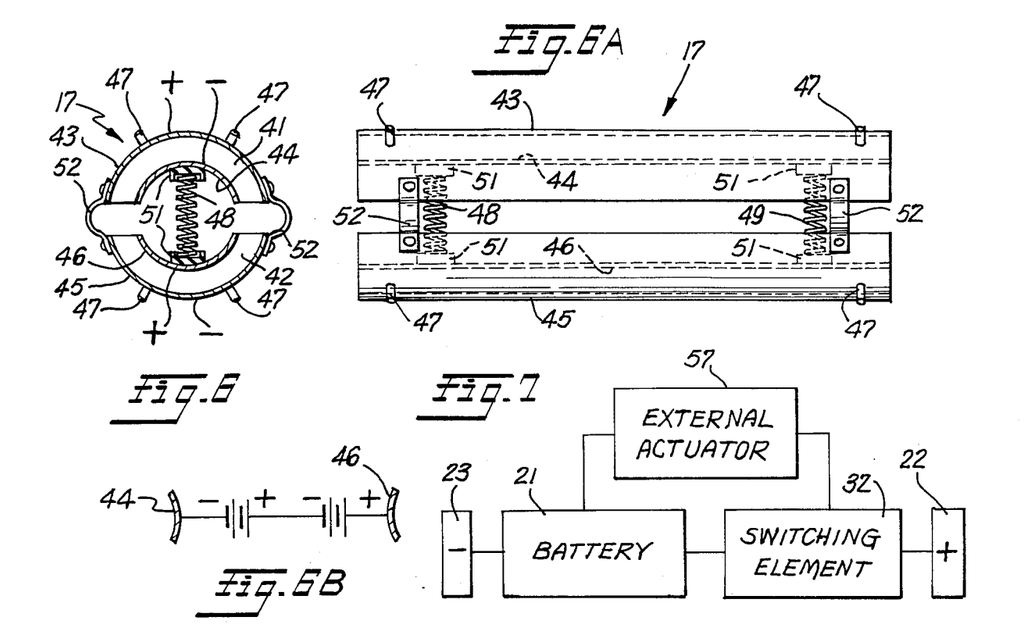
FIGS. 6, 6A, and 6B of the drawings illustrate still another embodiment of the invention wherein the birth control device is comprised of spaced-apart semicylindrical body members and wherein each semicylindrical body member can comprise either an inert electrode or a sealed battery.
FIG. 7 is a schematic block diagram of a system wherein a remotely actuated switch is employed to turn-on the birth control device.

FIGS. 6 and 6A of the drawings illustrate an embodiment of the invention which can be fabricated either as a self-contained, sealed battery type of birth control device 17 or alternatively as a capacitor-type electrode structure for excitation from an externally suppported battery for supplying the electrodes through a string-like conductor in the manner described in the preceeding paragraph. The birth control device 17 shown in FIGS. 6 and 6A is comprised by an elongated pair of opposed semi-cylindrical upper and lower body members 41 and 42. The upper body member 41 has an outer convex conductive surface 43 and an inner concave conducting surface 44 which opposes an inner concave conductive surface 46 on the lower semi-cylindrical body member 42 which also has an outer convex conductive surface 45. The space between the outer and inner conductive surfaces of the two semi-cylindrical body members 41 and 42 may be filled with an insulator if the device 17 is to be fabricated in the form of a set of inert electrodes for excitation from an outside battery through a string-like conductor as described above. Alternatively, the space between the outer and inner conductive electrode surfaces of the upper and lower body members 41 and 42 may hold the cells required to form a self-contained, sealed battery for developing an electric potential across the respective inner and outer conductive electrode surfaces of each of the body members 41 and 42.

In order to hold the birth control device shown in FIGS. 6 and 6A in place within the cervical canal, a plurality of projections shown at 47 are provided on the exterior convex surfaces of both the upper and lower semi-cylindrical body members 41 and 42. To bias the upper and lower body members 41 and 42 apart and maintain them in spaced-apart relationship as well as to insure engagement of the projections 47 with the side walls of the cervical canal, a set of resilient expansion springs 48 and 49 are provided at respective ends of the spaced-apart upper and lower members 41 and 42. Preferably, the expansion springs 48 are fabricated from an electrically insulating material; however, if not, insulating supports 51 are provided as shown in both FIGS. 6 and 6A between the ends of the spring and the inner conductive concave surfaces of the body members 41 and 42 so that the two opposed inner conductive surfaces can be maintained at different electric potentials thereby producing an electric field force between these two opposed conductive surfaces. The structure is completed by resilient spring-like conductive straps shown at 52 which electrically interconnect the outer conductive surfaces 43 and 45 of the upper and lower body members 41 and 42 and also serve to resiliently maintain the structure in assembled relation against the force of the expansion spring members 48 and 49.

FIG. 6B is a schematic electrical diagram illustrating the electrical interconnection between the upper and lower semi-cylindrical electrode members 41 and 42 whereby an enhanced electrostatic field force is produced in the space between the opposed spaced-apart, inner, concave, conductive electrode surfaces 44 and 46 for entrapment of male sperm. Assuming for the sake of discussion that each semi-cylindrical body member in fact comprises a battery cell capable of producing 1.5 volts between the respective conductive inner and outer electrode surfaces thereof, then the effect of interconnecting the outer electrode surfaces 43 and 45 via the resilient conductive strap members 52 will be as shown in FIG. 6B whereby the electromotive force produced between the inner, opposed concave electrode surfaces 44 and 46 will be combined to provide the desired 3 volt potential field value that prevents passage of sperm as discussed earlier in the specification.

In the event the device is used as an inert electrode structure and supplied from an external battery source of power through string-like conductors led to the device from externally supported batteries, the full 3 volts would be supplied across the two inner, opposed concave electrode conducting surfaces 46 and 44. Where the device is used as an externally supplied, inert electrode structure, the employment of duty cycle reduction techniques such as discussed with relation to FIGS. 4 and 5 would not be necessary. However, if the device is fabricated entirely self-contained with the two semi-cylindrical upper and lower body members 41 and 42 constituting sealed, electric potential developing battery cells, then the duty cycle reduction techniques and circuitry described with relation to FIGS. 4 and 5 could and should be employed for those devices where prolonged usage over several months is intended. It should be noted however, that with the device shown in FIGS. 6 and 6A, current drain reduction is achieved during dry periods of each month, since under such conditions, the inner, opposed concave conductive surfaces 44 and 46 would not normally engage body tissue so that conduction between the two surfaces would not occur where no cervical mucous or other fluid is present in the cervical canal.

A further embodiment of the invention is shown in FIG. 7 which is adapted for use with a birth control device as shown in FIGS. 2 and 3, or FIGS. 6 and 6A under conditions where the device of FIGS. 6 and 6A constitutes a self-contained sealed battery as explained above. In the system of FIG. 7, a remote or external actuator 57 is connected in circuit relationship with the battery 21 and switching element 32 for selectively turning-on switching element 32 and producing an electric field force with the birth control device under the external control of the user. The actuator 57 is fabricated in microminiaturized form and may comprise a sonic wave receiver, or the like, and which responds to signals generated by a small transmitter selectively operated by a user of the birth control device in advance of the mid month ovulating period. Actuator 57 is designed so that it can be turned-on or turned-off selectively by the user with the remotely controlled transmitter. Alternatively, the actuator could be controlled externally by the user through the use of an externally held switch whose controlling on-off output signals are supplied to actuator 57 via small diameter, string-like insulated conductor wires in the manner describe earlier.

Figure 8:
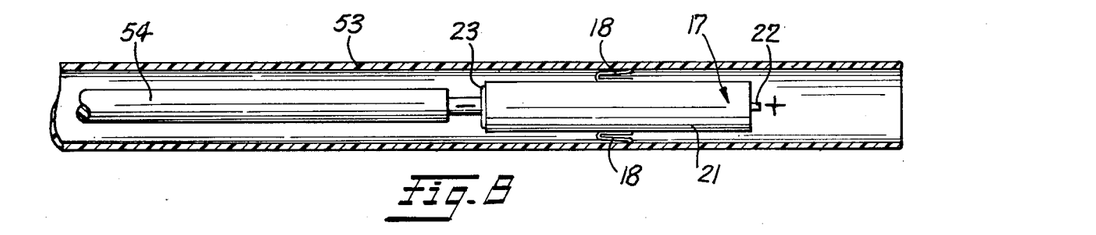
FIGS. 8 and 8A illustrate the manner in which a birth control device according to the invention is inserted in place within the cervical canal of a female.
Figure 8A:
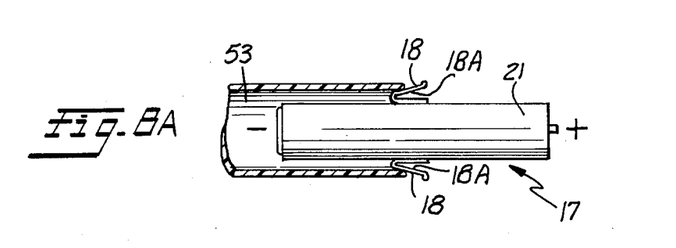

FIGS. 8 and 8A of the drawings illustrate a proposed technique for insertion of the birth control device 17 into the cervical canal and subsequent removal. It is proposed that only a skilled gynocologist perform and monitor this task. To insert the device, it is first mounted within an insertion tube 53 formed of a plastic and somewhat flexible material that is biologically inert or coated with biologically inert material whereby it can be safely used to perform the insertion. The birth control device 17 is inserted within the tube 53 with the anchoring prongs 18 thereof oriented in the direction shown in FIGS. 8 and 8A. A small flexible push rod 54 is run through the insertion tube 53 and is designed to extend along with the insertion tube 53 through the vaginal opening of the user and into the cervical canal. The insertion tube 53 then is inserted to a point within the cervical canal where the end thereof is properly located to deposit the birth control device at a desired location in the cervical canal. The push rod 54 then is manipulated so as to push the birth control device out of the end of the insertion tube and implace it in the cervical canal oriented in the manner shown in FIG. 1 of the drawings.

To extract the birth control device, the insertion tube 53 without push rod 54 again is reinserted through the vaginal opening into the cervical canal where the end of the tube will tend to surround the device in the manner shown in FIG. 8A of the drawings. It should be noted that the spring anchoring clips 18 have a somewhat tapered surface indicated at 18A which will be engaged by the end of the insertion tube 53 upon reinsertion of the insertion tube 53 in the manner indicated. It is this tapered surface 18A which will act as a cam surface to cam close the end of the spring clip 18 so as to withdraw the ends of the spring clips away from their anchoring position in the sides of the cervical canal. Thereafter, the insertion tube 53 with the birth control device 17 supported in the end thereof, is withdrawn.

If desired, the end of the insertion tube could include a small skirt or flap having appropriately positioned slots which would accomodate the anchoring spring clips 18 but otherwise normally would close the end of the insertion tube 53. With such a skirt or slotted flap surrounding the birth control device and embracing the spring clips, the end of insertion tube 53 will be substantially closed so that a vacuum then could be drawn at the remote end of the tube to assist in removal of the birth control device. Alternatively, the push rod 54 could be left in and the end thereof provided with remote actuated fingers, a magnet, a sticky adhesive surface or the like for grasping the end of the device 17 to assist in its removal.

From the foregoing description, it will be appreciated that the invention provides a new and improved method and device for birth control which employs introduction of an electrical force in the cervical canal of a female in such a way as to prevent impregnation by male sperm. The novel birth control method and means employs a set of battery operated, electrically conductive electrodes which when implanted within the cervical canal of the female and activated, produces an electrical force within the cervical canal that acts upon male sperm to impede and prevent the male sperm from migrating up the cervical canal and entering the uterine cavity thereby preventing fertilization of an egg in the fallopian tube.

INDUSTRIAL APPLICABILITY

The invention describes a new method and device for birth control for use with human females as well the female of most quadripeds and other vertebrates. The invention will find its greatest applicability within family planning activities of the medical profession.

Having described several embodiments of a new and improved method and device for birth control in accordance with the present invention, it is believed obvious that other modifications and variations of the invention will be suggested to those skilled in the art in the light of the above teachings. It is therefore to be understood that changes may be made in the particular embodiments of the invention described which are within the full intended scope of the invention as defined by the appended claims.

What is claimed is:

1. The method of birth control which comprises producing an electrical force within and about the cervical canal for preventing migration of male sperm through the cervical canal into the unterine cavity, said method comprising inserting a birth control device formed by a set of spaced-apart opposed low voltage electromotive force producing electrodes within at least the opening to the cervical canal and retaining it in place over extended periods of time and supplying an electromotive force of known voltage across the electrodes from an indepedent source of electric potential.

2. The method according to claim 1 wherein the birth control device for producing the electrical force is designed such that it does not substantially impede the free flow of menstrual and other fluid discharges through the cervical canal.

3. The method according to claim 2 wherein the birth control device includes a self contained sealed battery that provides the independent source of known electric potential and that is retained in place along with the electrodes for indefinite periods as long as desired by the user for birth control purposes.

4. The method according to claim 3 wherein the birth control device including the electrically conductive electromotive force producing electrodes are exposed to contact with any fluid within or about the cervical canal, the birth control device and said electrically conductive electrodes are fabricated from or covered by materials which are biologically inert and safe for physical contact with human and animal tissue over extended period of time, and the known electromotive force supplied across the electrodes is of the order of 3 volts.

5. The method according to claim 4 further including anchoring means attached to the birth control device and engaging the sides of the cervical canal for securely holding the device in place within the cervical canal.

6. The method according to claim 5 wherein a battery is used to energize the low voltage electrodes and the duty cycle on the battery is reduced by designing the birth control device to be maintained in an inactive state during periods when the cervical canal is dry, and wherein the electrically conductive electrodes are placed on the birth control device in a position where at least one of the electrodes does not normally engage tissue and maintains the battery in an inactive-off state unless exposed to fluid within the cervical canal to thereby reduce the duty cycle on the battery.

7. The method according to claim 6 wherein the electric force which acts on the male sperm and prevents its migration into the uterine cavity is in the form of an induced electric current flow through mucous fluid present in the cervical canal and/or electrostatic field forces acting on the sperm.

8. The method according to claim 7 further including sensing the temperature of the body of the user in whom the birth control device is implanted and activating the battery supplying the device to cause it to energize the electrode only upon the body temperature of the user reaching a predetermined higher than normal value.

9. The method according to claim 8 further including switching the battery energization of the electrodes between an inactive off and an energized on-state at a predesigned rate under conditions whereby the battery otherwise is enabled to supply electricity to the electrodes to thereby reduce the duty cycle on the battery further.

10. The method according to claim 7 further including switching the battery energization of the electrodes between an inactive off and an energized on-state at a predesigned rate under conditions whereby the battery otherwise is enabled to supply electricity to the electrodes to thereby reduce the duty cycle on the battery further.

11. The method according to claim 7 further including remotely switching the battery energization of the electrodes between an inactive off and an energized on-state and vice versa externally of the user's body with a remote controlled actuator whereby the battery selectively is enabled to supply electricity to the electrodes under the external control of the user of the birth control device.

12. The method according to claim 1 wherein the birth control device including the electrically conductive electromotive force producing electrodes are exposed to any fluid within or about the cervical canal, the birth control device and said electrically conductive electrodes being fabricated from or covered by materials which are biologically inert and safe for physical contact with human and animal tissue over extended periods of time.

13. The method according to claim 1 further including providing anchoring means attached to the birth control device for engaging the sides of the cervical canal and securely holding the device in place within the cervical canal.

14. The method according to claim 1 wherein a battery is used to energize the low voltage electrodes and the duty cycle on the battery supplying the device is reduced by designing it to be maintained in an inactive state during periods when the cervical canal is dry.

15. The method according to claim 14 wherein the electrically conductive electrodes are placed on the birth control device in a position where at least one of the electrodes does not normally engage tissue and maintains the battery supplying the device in an inactive-off state unless exposed to fluid within the cervical canal to thereby reduce the duty cycle on the battery.

16. The method according to claim 1 wherein the electric force which acts on the male sperm and prevents its migration into the uterine cavity is in the form of an induced electric current flow through mucous fluid present in the cervical canal and/or electrostatic field forces acting on the sperm.

17. The method according to claim 1 further including sensing the temperature of the body of the user in whom the birth control device is implanted and activating the source of electric potential supplying the device to cause it to energize the electrode only upon the body temperature of the user reaching a predetermined higher than normal value.

18. The method according to claim 1 further including switching the energization of the electrodes between an inactive off and an energized on-state at a predesigned rate under conditions whereby the electrodes otherwise are enabled to produce an electrical force within the cervical canal.

19. The method according to claim 1 further including remotely switching the energization of the electrodes between an inactive off and an energized on-state and vice versa externally of the user's body with a remotely controlled actuator whereby the electrodes selectively are enabled to produce an electrical force within the cervical canal under the external control of the user of the birth control device.

20. A birth control device comprising a set of low voltage, opposed electromotive force producing eletrodes designed and proportioned to be inserted in proximity to the cervical canal of a female human or animal for producing an electrical force within the cervical canal for acting on male sperm and preventing migration of the sperm through the cervical canal and into the uterine cavity, means for supplying an electromotive force of known voltage across the electrodes from an independent source of electric potential, and means for fixing the birth control device in proximity to the cervical canal, said birth control device including the means for fixing the same being fabricated from or coated by materials which are biologically inert and safe for physical contact with human and animal tissue over extended periods of time.

21. The birth control device according to claim 20 wherein the device including the means for fixing the same are designed, shaped and proportioned so that the device does not substantially impede or prevent free flow of menstrual and other fluid discharges through the cervical canal.

22. The birth control device according to claim 21 wherein the device includes a self contained sealed battery for energization of the electromotive force producing electrodes and can be retained in place in proximity to the cervical canal for indefinite periods as long as desired by the user for birth control purposes.

23. The birth control device according to claim 20 wherein the device including the electrically conductive electromotive force producing electrodes are designed to be exposed to any fluids within the cervical canal.

24. The birth control device according to claim 22 wherein the device including the electrically conductive electromotive force producing electrodes are designed to be exposed to any fluids within the cervical canal.

25. The birth control device according to claim 23 wherein the electrically conductive electrodes are placed on the birth control device in a position where at least one of the electrodes does not normally engage tissue and maintains the independent source of electric potential supplying the device in an inactive-off state unless exposed to fluid within the cervical canal to thereby reduce the duty cycle on the battery.

26. The birth control device according to claim 24 wherein the electrically conductive electromotive force producing electrodes are placed on the birth control device in a position where at least one of the electrodes does not normally engage tissue and maintains the battery in an inactive-off state unless exposed to fluid within the cervical canal to thereby reduce the duty cycle on the battery.

27. The birth control device according to claim 20 wherein the electromotive force produced by the electrodes results primarily in an induced electric current flow through the mucous fluid present in the cervical canal and prevents migration of the sperm through the cervical canal to the uterine cavity.

28. The birth control device according to claim 26 wherein the electromotive force produced by the electrodes results primarily in an induced electric current flow through the mucous fluid present in the cervical canal and prevents migration of the sperm through the cervical canal to the uterine cavity.

29. The birth control device according to claim 20 wherein the electromotive force produced by the electrodes results primarily in an electrostatic field acting on the sperm to prevent their migration through the cervical canal to the uterine cavity.

30. The birth control device according to claim 26 wherein the electromotive force produced by the electrodes results in an electrostatic field acting on the sperm to prevent their migration through the cervical canal to the uterine cavity.

31. The birth control device according to claim 28 wherein the electromotive force produced by the electrodes also results in a substantial electrostatic field acting on the sperm to prevent their migration through the cervical canal to the uterine cavity.

32. The birth control device according to claim 20 wherein the device has an elongated cylindrical configuration and is formed by a pair of opposed, spaced-apart semi-cylindrical body members whose outer convex and inner concave surfaces are coated with electrically conductive material to form the electromotive force producing electrodes, the concave conducting surfaces of the body members being spaced-apart and held in opposing assembled relation by insulating resilient spring means, means for electrically interconnecting the two outer electrically conductive convex surfaces in series electrical circuit relationship whereby an increased electrostatic field force is produced in the space between the two spaced-apart opposing concave conductive surfaces of the device, and wherein the means for anchoring the device within the cervical canal comprises a plurality of projections formed on the exterior convex surfaces of the opposed semi-cylindrical body members.

33. The birth control device according to claim 31 wherein the device has an elongated cylindrical configuration and is formed by a pair of opposed, spaced-apart semi-cylindrical battery body members whose outer convex and inner concave surfaces are coated with electrically conductive material to form the electrodes for the respective batteries thus shaped, the concave conducting surfaces of the body members being spaced-apart and held in opposing assembled relation by insulating resilient spring means, means for electrically interconnecting the two batteries thus formed in series electrical circuit relationship whereby an increased electrostatic field force is produced in the space between the two spaced-apart opposing concave conductive surfaces of the batteries, and wherein the means for anchoring the device within the cervical canal comprises a plurality of projections formed on the exterior convex surfaces of the opposed semi-cylindrical battery bodies.

34. The birth control device according to claim 20 further including body temperature sensing means fabricated in microcircuit form mounted along with the device in the body of the user in whom the birth control device is implanted, and microconductor means interconnecting the temperature sensing means with the electrodes for controlling energization of the electrodes by a source of low voltage and causing the source of low voltage to supply excitation voltage to the electrodes only upon the body temperature of the user reaching a predetermined higher than normal temperature.

35. The birth control device according to claim 31 further including body temperature sensing means fabricated in microcircuit form on the device for mounting in the body of the user in whom the birth control device is implanted, and microconducter means interconnecting the temperature sensing means with the electrodes for controlling energization of the electrodes by the battery and causing the battery to supply excitation voltage to the electrodes only upon the body temperature of the user reaching a predetermined higher than normal temperature.

36. The birth control device according to claim 32 further including body temperature sensing means formed on the device for implantation within the body of the user, microconductor means interconnecting the temperature sensing means with the electrodes for controlling energization of the electrodes by a source of low voltage and causing the source of low voltage to supply excitation voltage to the electrodes only upon the body temperature of the user reaching a predetermined higher than normal temperature.

37. The birth control device according to claim 33 further including body temperature sensing means formed on the device for implantation within the body of the user, and microconductor means interconnecting the temperature sensing means with the electrodes and the battey for controlling energization of the electrodes by the battery and causing it to supply excitation voltage to the electrodes only upon the body temperature of the user reaching a predetermined higher than normal temperature.

38. The birth control device according to claim 20 further including microminiaturized switching means interconnecting the electrodes to a battery for electrically controlling application of an excitation voltage to the electrodes at a predesigned rate to thereby reduce the duty cycle on the battery.

39. The birth control device according to claim 28 further including microminiaturized switching means interconnecting the electrodes to the battery for electrically controlling application of an excitation voltage to the electrodes at a predesigned rate to thereby reduce the duty cycle on the battery.

40. The birth control device according to claim 37 further including microminiaturized switching means interconnecting the electrodes to the battery for electrically controlling application of an excitation voltage to the electrodes at a predesigned rate to thereby reduce the duty cycle on the battery.

41. The birth control device according to claim 20 further including externally actuated switching means selectively operated by a user of the birth control device for remotely switching energization of the electrodes between an inactive off and an energized on state and vice versa.

42. The birth control device according to claim 40 further including externally activated switching means selectively operated by a user of the device for remotely controlling turn-on and turn-off of the battery supply of electric potential to the electrodes.

43. The birth control device according to claim 20 wherein the device is designed to be seated within a small diameter tube having a push rod for extraction of the device from the end of the tube and insertion of the device in place in the cervical canal of a female human or animal.

44. The birth control device according to claim 42 wherein the device is designed to be seated within a small diameter tube having a push rod for extraction of the device from the end of the tube and insertion of the device in place in the cervical canal of a female human or animal.

* * * * *